United States Patent [19]

Hsien

[11] Patent Number: 4,860,953

[45] Date of Patent: Aug. 29, 1989

[54] AESTHETICALLY PLEASING AIR FRESHENER

[76] Inventor: Simon Hsien, No. 29-26, Che Lu Chien, Pao An Tsun, Jen Te Hsiang, Tainen Hsien, Taiwan

[21] Appl. No.: 272,914

[22] Filed: Nov. 18, 1988

[51] Int. Cl.⁴ .............................................. A24F 25/00
[52] U.S. Cl. ....................................... 239/47; 239/55; 239/211
[58] Field of Search ................... 239/34, 47, 53–59, 239/211

[56] References Cited

U.S. PATENT DOCUMENTS

| | | | |
|---|---|---|---|
| 2,811,808 | 11/1957 | Briese | 239/211 |
| 3,016,199 | 1/1962 | Keydel | 239/55 |
| 3,134,544 | 5/1964 | Copley | 239/55 |
| 3,730,434 | 5/1973 | Engel | 239/47 |

Primary Examiner—Andres Kashnikow
Assistant Examiner—Patrick N. Burkhart
Attorney, Agent, or Firm—Morton J. Rosenberg

[57] ABSTRACT

This invention relates to a miracle air freshener and in particular to one having a can which has a dried compressed sponge, several pieces of fragrance, a soft wood and a figure. When we pour water into the can, the sponge will absorb water and expand several times of its compressed size and forces the figure strectched out of the can to beautify the place.

6 Claims, 6 Drawing Sheets

AESTHETICALLY PLEASING AIR FRESHENER

BACKGROUND OF THE INVENTION

Prior art air fresheners have generally been provided in containers such as bottles which only differ in overall contour such as being rectangular, square or rounded. Additionally, such prior art air fresheners contain a liquid or solid fragrance material therein. Such prior art air fresheners thus have a singular function which is to freshen the air however, such do not provide for a system which allows for both freshening the surrounding environment while simultaneously providing an aesthetically pleasing system which may be placed in the home or a vehicle. Thus, the subject aesthetically pleasing air freshener includes an object maintained within a closed can which may be opened by a tap member. Additionally, when liquid which may be in the compositional form of water is inserted into the open can, the object emerges from internal the can to provide a decorative element. Fragrance maintained within the can allows for the air freshening function of the overall air freshener system.

SUMMARY OF THE INVENTION

An air freshener system which includes a can member having a recessed channel formed on an external surface thereof. The can includes a tap opening member for releasably securing the cover to the can body. A dried compressed sponge layer is located adjacent the bottom of the can and a resilient layer is positionally located on the dried compressed sponge. A layer of fragrance composition is spread on the resilient soft layer and an object having a stem is inserted within the resilient soft layer. Thus, when water is poured into the can, the sponge absorbs the water and displaces the object in an upward direction for viewing by an external user.

It is the primary object of the subject invention to provide an air freshener system which is aesthetically pleasing and beautifies a room or the interior of a vehicle.

It is a further object of the present invention to provide an air freshener system which allows for fragrance composition to be emitted into the surrounding environment.

It is a further object of the subject invention to provide an air freshener system which is of low cost to produce and manufacture.

It is a further object of the subject invention to provide an air freshener system which is easy to manufacture and has few moving elements.

Other important features and advantages of the invention will become apparent during the course of the following detailed description.

DETAILED DESCRIPTION OF THE PREFERRED EMBODIMENTS

Figure 1:
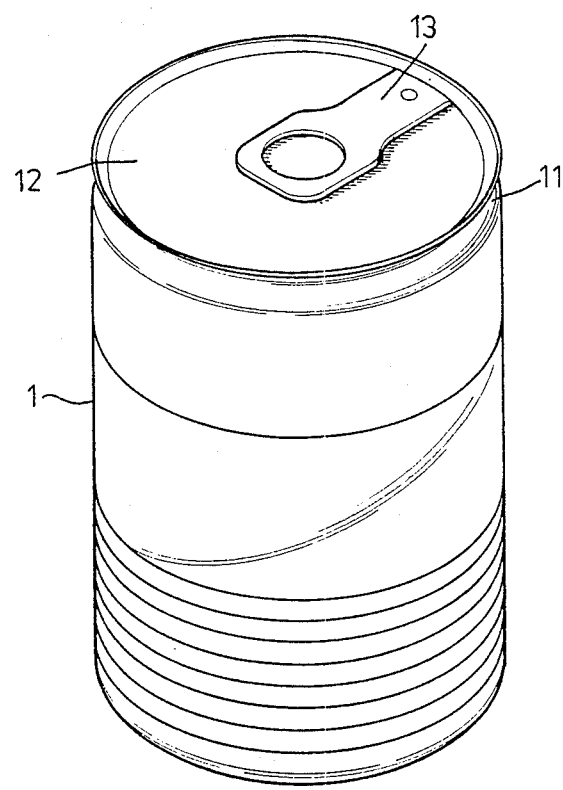
FIG. 1 is a perspective view of the subject air freshener system showing the external view of the closed can member as it is viewed prior to use.

Referring now to FIG. 1 there is shown a perspective view of the aesthetically pleasing air freshener system which includes can 1 having cover 12 mounted thereon to provide a closed internal volume for containing object 5 as will be described in following paragraphs. Can 1 is generally cylindrical in contour as is clearly seen in FIG. 1 and provides for recess trough or channel 11 formed at an upper portion thereof which allows for maintaining cover 12 in a releasably closed manner as is clearly seen in FIG. 2. Tap member 13 is mounted on cover 12 and allows the user to remove cover 12 in a manner coincident with the removal of well known can tops. By lifting tap 13 in an upward manner, cover 12 is pulled away from the remaining body portion of can 1 and provides access to object 5 contained within can 1.

Figure 2:
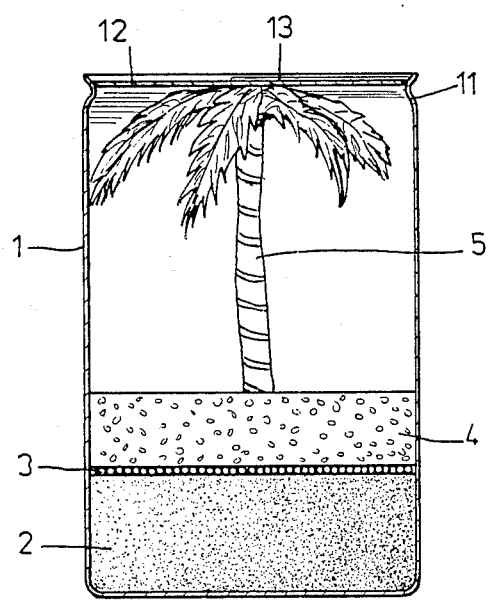
FIG. 2 is a cross-sectional view of the subject air freshener system showing an object maintained in the closed can prior to use.

Referring now to FIG. 2 it is clearly seen that the elements comprising the internal structure of the air freshener system includes a dried compressed sponge member 2 which defines a layer member adjacent the bottom of can 1. Fragrance layer 3 is positionally located on the top surface of dried compressed sponge member 2. Fragrance compositions are well known in the art and are used in prior art air freshener systems.

Figure 3:
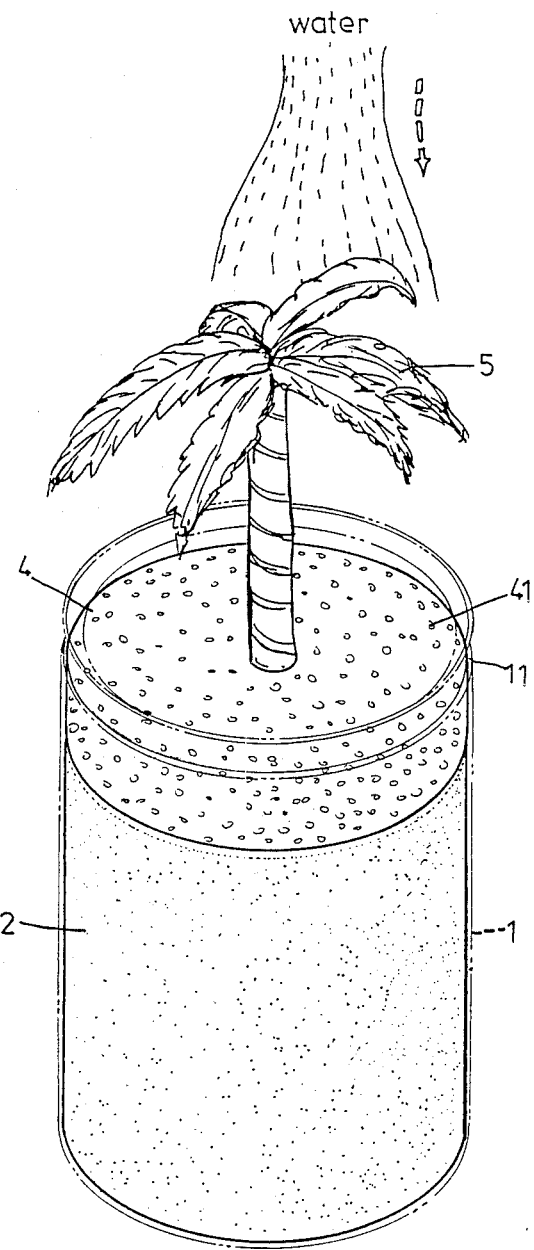
FIG. 3 is a perspective view of the subject air freshener system showing expansion of a sponge layer as liquid is applied to the open can.

On top of compositional layer 3 there is provided a layer of a soft resilient material which may be of a plastic composition or formed of a soft wood layer 4.

Where resilient layer 4 is formed of a soft wood composition, holes 41 may be drilled therein as shown in FIG. 3 to allow moisture to pass therethrough and further to allow fragrances from fragrance layer composition 3 to be emitted to the external environment.

As shown in FIG. 3 when liquid which generally may be in the form of water is poured internal to can 1, dried and compressed sponge layer 2 absorbs the liquid and expands several times its original volume size, thus forcing object 5 to be displaced in an upward direction. Recess trough or channel 11 prevents object 5 from emerging from can 1 as object 5 rises since the layer of compressed sponge 2 which has now absorbed the water or liquid moves in an upward direction and contacts the internal edge of recess trough 11. Thus, sponge 2 does not pass external to can 1 and maintains object 5 in fixed position within can 1.

Figure 4:
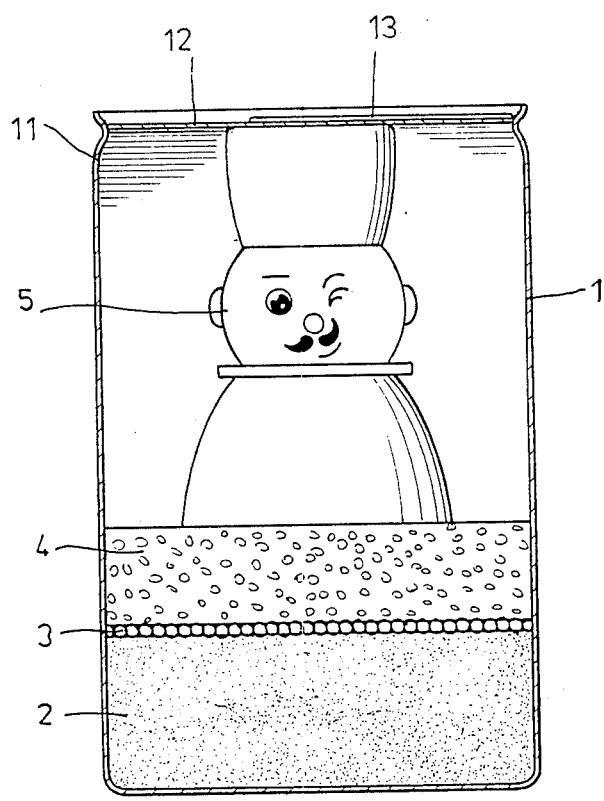
FIG. 4 is a cross-sectional view of an embodiment of the subject air freshener system showing an object contained within the closed can which has a different contour than the object provided in the preferred embodiment of FIG. 2.
Figure 5:
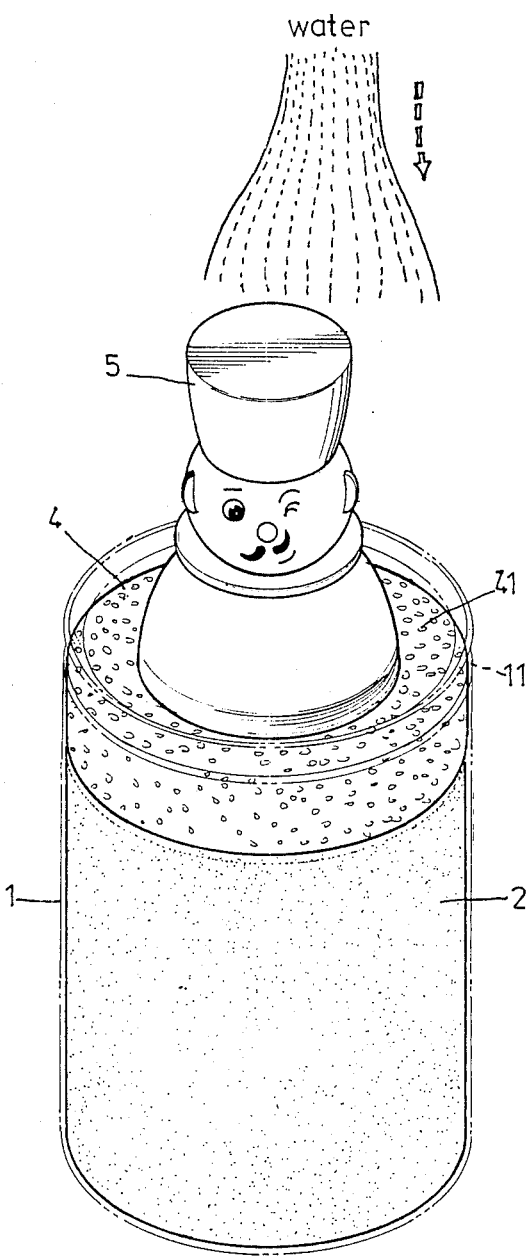
FIG. 5 is a perspective view of the embodiment of the subject invention shown in FIG. 4 subsequent to the can cover being removed and liquid being applied; and, FIG. 6 is a perspective view of a prior art air freshener system.

Object 5 may be of differing contours and as shown in FIGS. 2 and 3, object 5 is in the form of a palm tree. In FIGS. 4 and 5, object 5 takes the contour of a joker or clown however, the particular contour of object 5 may be formed at the direction of the user.

The resilient layer 4 may be formed of a soft wood as has been described, or may be of a plastic composition such as polyethylene or other like material compositions.

Figure 6:
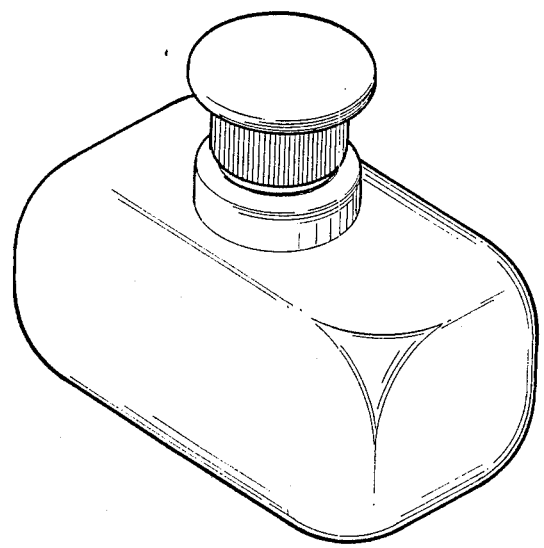

Referring to FIG. 6, such merely shows a view of the prior art which is in the form of a bottle having a singular function as an air freshener and does not provide for an aesthetically pleasing air freshener system as is herein described.

I claim:

1. An air freshener system comprising a can member having an internal volume and an internally directed recess trough volume and an internally directed recess trough member, a tab member, a cover member releasably secured to an upper end of said can member, said tab member secured to an upper surface of said cover member, a dried compressed sponge layer located adjacent a bottom portion of the can member, a resilient layer positionally located on the dried compressed sponge layer, a layer of fragrance composition located on the resilient layer, and an object having a stem member inserted within the resilient layer, whereby when liquid is poured into the can member, the dried sponge layer absorbs the liquid resulting in an expression in the volume of the sponge layer for displacing the object in an upward direction.

2. The air freshener system as recited in claim 1, wherein the cover member is removable from the can member by lifting the tab member.

3. The air freshener system as recited in claim 1 or 2, wherein said internally directed recess trough member provides a blocking stop portion to prevent the liquid impregnated sponge layer from expanding external the can member.

4. The air freshener system as recited in claim 1, wherein said object may be of varying contour.

5. The air freshener system as recited in claim 1, wherein the resilient layer may be formed of a soft wood composition or plastic material composition.

6. The air freshener system as recited in claim 1 or 5, wherein said resilient layer has a plurality of holes formed therein for permitting fragrance odors to pass therethrough.

* * * * *